United States Patent [19]
Menger et al.

[11] Patent Number: 6,143,534
[45] Date of Patent: Nov. 7, 2000

[54] MICROBIAL PROCESS FOR PRODUCING METHANE FROM COAL

[75] Inventors: William M. Menger; Ernest E. Kern, both of Houston, Tex.; O. C. Karkalits, Lake Charles, La.; Donald L. Wise, Belmont, Mass.; Alfred P. Leuschner; David Odelson, both of Cambridge, Mass.; Hans E. Grethlein, Lansing, Mich.

[73] Assignee: Reliant Energy Incorporated, Houston, Tex.

[21] Appl. No.: 07/814,078

[22] Filed: Dec. 24, 1991

Related U.S. Application Data

[63] Continuation of application No. 07/686,271, Apr. 15, 1991, abandoned, which is a continuation of application No. 07/156,532, Feb. 16, 1988, abandoned, which is a continuation-in-part of application No. 06/693,028, Jan. 22, 1985, Pat. No. 4,826,769, and a continuation-in-part of application No. 06/816,289, Jan. 6, 1986, Pat. No. 4,845,034.

[51] Int. Cl.$^7$ ................................................. C12P 5/02
[52] U.S. Cl. ....................... 435/167; 435/252.4; 210/603; 48/210
[58] Field of Search ................. 435/167, 252.4; 210/603; 48/210, DIG. 6

[56] References Cited

U.S. PATENT DOCUMENTS

| | | | |
|---|---|---|---|
| 3,540,983 | 11/1970 | Rose et al. | 435/255 |
| 3,640,846 | 2/1972 | Johnson | 210/603 |
| 3,826,308 | 7/1974 | Compere-Whitney | 435/166 X |
| 4,187,148 | 2/1980 | Reijoner | 435/167 X |
| 4,356,269 | 10/1982 | Thomsen et al. | 435/316 |
| 4,358,537 | 11/1982 | Chynoweth | 435/167 X |
| 5,670,345 | 9/1997 | Srivastava et al. . | |

OTHER PUBLICATIONS

"Alkaline Hydrolysis Transformation of Coal", Electric Power Research Institute Report EPRI AP–4585, Research Project 2655–2 (May 1986).

"The Digestive System", Ch. Noirot & C. Noirot–Timothee, p. 49–87.

"Food and Feeding Habits of Termites", T.G. Wood, *Production Ecology of Ants and Termites,* pp. 55–58 (1978).

"Feeding Relationships and Radioisotope Techniques", Elizabeth A. McMahan, *Biology of Termites,* vol. 1, pp. 387–406 (1969).

Lee, K. E., "Termites and Soils", p. 128–145 (1971).

Condensed Chemical Dictionary, p. 516, 661, 1974.

French et al, Mater Org (Berl) 10(4), 1975. p. 281–288.

Lee et al., *Curr. Microbiol.* 15(6), p. 337–342, 1987.

O'Brien et al, *Aust J. Biol. Sci*, 35, p. 239–262, 1982.

Odelson et al., Appl. Environ. Microbiol. 49(3) p. 614–621, 1985.

Healy et al, App. Envoir. Microbiol., Jul., 1979, vol. 38, pp. 84–89.

Colberg et al, App. Envir. Microbiol, 49(2), Feb. 1985, pp. 345–349.

Cohen et al, App. Envir. Microbiol. 44(1), Jul. 1982, pp. 23–27.

Benner et al. App. Envir. Microbiol. 47(5), May 1984, pp. 998–1004.

Benner et al, App. Enivr. Microbiol. 50(4), Oct. 1985, pp. 971–976.

*Primary Examiner*—Irene Marx
*Attorney, Agent, or Firm*—Bracewell & Patterson, L.L.P.

[57] ABSTRACT

Lignite is treated with ligninase source to enhance its reactivity. In one embodiment, lignite is gasified in a subterranean reactor by simultaneous digestion by anaerobic ligninase producers, such as termite microflora, and acid formers and methanogens. In another embodiment, the lignite is treated with ligninase prior to digestion by the acid formers and methanogens. If desired, the lignite may be pretreated by alkaline hydrolysis.

9 Claims, 8 Drawing Sheets

MICROBIAL PROCESS FOR PRODUCING METHANE FROM COAL

CROSS-REFERENCE TO RELATED APPLICATION:

This is a continuation of co-pending application Ser. No. 686,271 filed on Apr. 15. 1991, now abandoned, which is is a continuation application of Ser. No. 156,532 filed on Feb. 16, 1988 now abandoned, which is is a continuation-in-part of U.S. patent application Ser. No. 693,028 filed Jan. 22, 1985 now U.S. Pat No. 4,828,769, and U.S. patent application Ser. No. 816,289 filed Jan. 6, 1986 now U.S. Pat. No. 4,845,034, both copending herewith.

FIELD OF INVENTION

This invention relates to the biochemical reaction of a substrate with microorganisms to produce combustible gases. More particularly, this invention relates to producing fuel gas from lignin substrates such as coal using ligninase-producing, acid forming and methanogenic microorganisms.

BACKGROUND OF THE INVENTION

Although the utilization of coal to produce mechanical and electrical energy through combustion provides a fundamental contribution to our energy needs, this technology suffers certain limitations. These limitations arise through concern about the environmental effects of combustion, through inefficiencies and excessive costs involved in transporting and burning certain coals, and because the universal technique of steam generation imposes a localized utilization of steam at the time of generation. These considerations have stimulated much effort to develop processes for the conversion of coals into fuel gas, a storable, readily transported form of fuel. Gasification of coal can overcome or mitigate many of the objections raised, but current gasification technology is, in turn, not free of problems. Paramount is the enormous capital cost projected for conventional coal gasification plants. This cost makes the product gas expensive. The expense is a reflection of the cost of massive high temperature chemical reaction vessels capable of withstanding high pressures and the cost of catalytic reactors susceptible to contaminant poisoning. Accordingly, the present state of the art of thermal gasification of coal leaves considerable room for improvement.

On the other hand, many useful products have been obtained by the action of microbial organisms in the digestion of carbohydrates, such products including ethanol, insulin by genetically altered microorganisms, and methane from the anaerobic digestion of biomass. Because of the slow growth or action of the microbes, it is often necessary to use a large reactor to produce biochemical reaction products in commercially significant quantities. Often, startup times ranging up to several months are required for the microbes to grow to achieve a sufficient population density in the substrate to produce usable quantities of the desired biochemical products. Further, conditions for the microorganisms, including temperature, pH and toxic substance concentrations, must be maintained within critical limits to avoid killing the microbes. Thus, if such conditions are not maintained, mortality of the microorganisms will result and their growth must be reinitiated.

In the conversion of substrates to methane in commercially significant quantities, the above problems are particularly acute because of the large volumes of substrate and methane involved. Much effort has been directed to providing suitably economic reactors for the conversion of various substrates into methane. For example, U.S. Pat. No. 4,356,269 describes a semisubmerged insulated apparatus which has a preheating chamber provided with a heating device, a gas processing chamber in which the microorganisms are grown, and a storage chamber for spent manure.

The anaerobic digestion of a substrate is typically a three-step process in which complex organic materials are converted to the end products of methane and carbon dioxide. In the initial steps, complex organic molecules are converted into substances such as propionate, butyrate, valerate, lactate, formate and ethanol, and eventually into acetate. The organisms responsible for this conversion are collectively termed acid formers and may be either anaerobic or facultative in nature. The final step, conversion of acetate to methane and carbon dioxide, is performed by organisms collectively termed methane formers, or methanogens, which are strictly anaerobic. Because the methanogens generally grow more slowly than do the acid formers, the final step of the process is generally considered the rate limiting step. Generally, conversion of a complex organic substrate yields a gas which is typically fifty to seventy percent methane and thirty to fifty percent carbon dioxide.

In the biogasification of coal and other substrates containing macromolecular substances, however, the substrate is not readily amenable to digestion by acid formers and methanogens. Acid formers are generally unable to convert the high molecular weight substances, especially those containing fused aromatics such as coal, for example, into the lower molecular weight acids required by the methanogens. Thus the development of technology for the biogasification of coal and other macromolecular substances requires an acceptable means of treating such substrates prior to the more familiar digestion with acid formers and methanogens used in the gasification of other less complex substrates.

It has been reported to subject coal to alkaline hydrolysis in order to break down the physical and chemical structure of the coal to make it more accessible to microbial action, for example, to upgrade the coal by biological removal of nitrogen and sulfur contaminants. For instance, it was reported that milled subbituminous coal was subjected to alkaline hydrolysis at 200–300° C. for 30–60 minutes with 0–20% sodium carbonate on a coal volatile solids basis in "Alkaline Hydrolysis Transformation of Coal," Electric Power Research Institute Report EPRI AP-4585, Research Project 2655-2 (May 1986). Such alkaline hydrolysis of coal is also disclosed in aforementioned patent applications, U.S. Ser. Nos. 693,028 and 816,289, which are hereby incorporated herein by reference. Also, disclosed in said applications are reactors, conditions and microorganisms for the biogasification of coal such as lignite and the alkaline hydrolysis products thereof.

It has also been reported that some aerobic microorganisms may degrade lignin structures in coal. However, it has been shown that such organisms require a very controlled diffusion of oxygen, and it is difficult to maintain the coal at the proper conditions for such degradation.

It has also been known that symbiotic microorganisms inhabit the digestive system of some higher organisms and aid in the digestive process. For example, it is well-known that termites can dissociate wood, which consists primarily of lignin, hemicellulose, and cellulose. Anaerobic degradation of wood by termites has been attributed to the symbiotic microorganisms which inhabit the termite's digestive system and which are apparently crucial for the insects' survival. The digestive tract of termites consists of three major sections: The foregut, the midgut, and the hindgut [Noirot, C. and C. Noirot-Timothee, "The Digestive System," in K. Krishna and E. M. Weesive (Eds.), *Biology of Termites*, pp. 48–88 (Academic Press, N.Y., N.Y. 1969)]. It has been suggested that termites "pretreat" wood in their foregut and then convert the pretreated substrate to food in their hindgut. The bulk of the symbiotic microbiota are contained in the hindgut. The pretreatment may be accomplished by enzymes produced by the microorganisms, at least one of which serves to break down the lignin to smaller molecules. The class of enzymes which dissimilate lignin are generally known as "ligninases".

Up to 83% of the wood-lignin, 99% of the wood-cellulose, and 93% of the wood-hemicellulose has been reported to be degraded by termites in Wood, T. G., "Food and Feeding Habits of Termites," in *Production Ecology of Ants and Termites*, M. V. Brian (ed) pp. 55-8 (Cambridge Univ. Press., Cambridge, United Kingdom 1978). The extent of lignin decomposition varies widely among termites as reported therein:

| Termite | Food | % Lignin Degraded |
|---|---|---|
| Lower Termites: | | |
| Calotermes sp. | wood | 2–26 |
| Heterotermes sp. | " | 14–40 |
| Reticulitermes sp. | " | 70–83 |
| Hodotermes sp. | red grass | 0.3 |
| Higher Termites: | | |
| Nasutitermes s. | wood | 42–82 |

Although the majority of termites feed on wood, some species having a decided preference for leaves, grass, humus, and dung have been reported in McMahan, E., *Feeding Relationships in the Biology of Termites*, K. Drishna and F. Weesner (eds.) pp. 387–406 (Academic Press, New York, N.Y. 1969) and Lee, E. and T. G. Wood, *Termites and Soils* (Academic Press London 1971). All of these foods are rich in lignin, hemicellulose, and cellulose.

SUMMARY OF THE INVENTION

The present method involves the use of ligninase to assist in the biochemical reaction of lignin substrates such as coal. In one aspect of the invention, there is provided a method for biochemically converting lignin substrate to gaseous fuel which includes the steps of: (1) preparing a medium containing lignin substrate and suitable for sustaining anaerobic microorganisms; (2) inoculating the medium with microorganisms including anaerobic ligninase producers, acid formers and methanogens; (3) culturing the microorganisms to biochemically reduce at least a part of the substrate to methane; and (4) recovering methane from the medium. Preferably, the lignin substrate is a coal such as lignite, and the innoculant includes termite microflora. If desired, the coal may be pretreated by alkaline hydrolysis.

In another aspect of the invention, there is provided a method of treating coal for biochemical reaction which includes contacting the coal with a ligninase at reactive conditions and for a time effective to substantially degrade the coal. The ligninase is preferably obtained from termite microflora, and may be placed in contact with the coal as ligninase per se, or produced by the growth of termite microflora or other anaerobic ligninase producers in the mixture. If desired, the coal may be pretreated by, for example, alkaline hydrolysis, or the ligninase-coal contact may occur conjointly with other bioreaction of the substrate, such as, for example, the growth of acid forming and methanogenic microorganisms in the mixture.

DETAILED DESCRIPTION OF THE PREFERRED EMBODIMENTS

In one aspect of the present invention, there is provided a method for treating lignin substrate with an enzyme, and in another the biogasification of lignin substrate is assisted by the treatment of the substrate with the enzyme. An important aspect of this enzyme treatment is the use of an enzyme to break down or assist in the breakdown of larger molecules in the lignin substrate to facilitate the anaerobic digestion of the substrate by microorganisms. Enzymes contemplated as suitable in the method broadly include the class of enzymes known as "ligninases" which are effective to cleave chemical bonds in lignin and lignin-related substances. As used herein, the term "lignin substrate" refers to lignin itself and substrates containing lignin and/or lignin-related substances which contain a fused plurality of the lignin moiety:

wherein X is hydroxyl or an ether oxygen and Y is hydrogen or methoxy. "Lignin substrate" is also used in a broad sense to include substrates containing substances which are broken down by the ligninases. A preferred lignin substrate is coal which, for the purpose of this invention is inclusive of carbonized or coalified vegetable material including peat, lignite, sub-bituminous coal, bituminous coal and anthracite coal which is at least partially degradable by ligninase.

Any source of ligninase is contemplated as being suitable in one or more embodiments of the invention, such as, for example, ligninase obtained from a wood fungus such as *Phanerochaete chrysosporium*. However, in one embodiment it is preferred to use an anaerobic microorganism as the ligninase source. A preferred source of such ligninases is termite microflora. As used herein, "termite microflora ligninase" includes lignolytically active enzymes obtained from termite microflora and lignolytically active analogs, homologues, isomers, mutants, fragments or derivatives thereof, regardless of their source or synthesis. It is contemplated that the ligninase may be used in the form of viable termites, whole termites and homogenates thereof, termite intestinal tracts and portions or homogenates thereof, cultures obtained by the growth of microflora obtained from any of these sources, and enzymes extracted from such sources and such cultures, and the like. A particularly preferred source of the enzyme is the digestive tract homogenate of termites, and cultures obtained from a lignite medium using this homogenate as the inoculum.

Representative termite species include the lower termites, such as, for example, *Aderitotermes* sp., *Trinervitermes* sp., *Calotermes* sp., *Heterotermes aureus*, *Reticulitermes tibialis*, *Hodotermes* sp., *Coptotermes lacteus*, *Kelotermes* sp., *Zootermopsis nevadensis*, *Zootermopsis laticeps*, *Incisitermes* sp., *Pterotermes* sp., *Marginitermes hubbardi*, *Mastotermes darwiniensis*, *Paraneotermes simplicornus*, and the like. Particularly preferred are the higher termites, such as, for example, *Nasutitermes exitisus*, *Nasutitermes nigriceps*, *Nasutitermes costalia*, *Cubitermes severus*, *Microcerotermes* sp., *Procubitermes* sp., *Anopolotermes* sp., *Gnathamitermes* sp., and the like.

In the present invention, the lignin substrate is treated by contact with a ligninase source. The ligninase functions to break down the substrate by cleavage at the lignin moieties. In a preferred embodiment, the molecular weight of the substrate is substantially reduced, although this is not always necessary or possible. For example, a lignin moiety may be held in the macromolecular structure of the substrate by bonds which are not subject to the lignolytic activity of the enzyme, as well as bonds which are cleaved by the ligninase. Thus, cleavage of such bonds by the ligninase may increase the reactivity of the resulting substrate, or make it more suitable for digestion by acid formers and/or methanogens, without actually releasing lower molecular weight compounds. In any case, a beneficiation of the substrate by the enzyme can be observed as an increase in the conversion or rate of conversion upon subsequent or concurrent digestion of the substrate by acid formers relative to digestion of the substrate under identical conditions without such enzymatic treatment.

The enzyme and/or enzyme-producing microorganisms may be employed consecutively or simultaneously with other microorganisms such as acid formers and methanogens to gasify the substrate in a subterranean cavity (FIGS. 1 and 2) or another suitable reactor, or used to treat a substrate, for example, prior to subterranean bioreaction thereof (FIGS. 3 and 4) as discussed in more detail hereinbelow.

Figure 6:
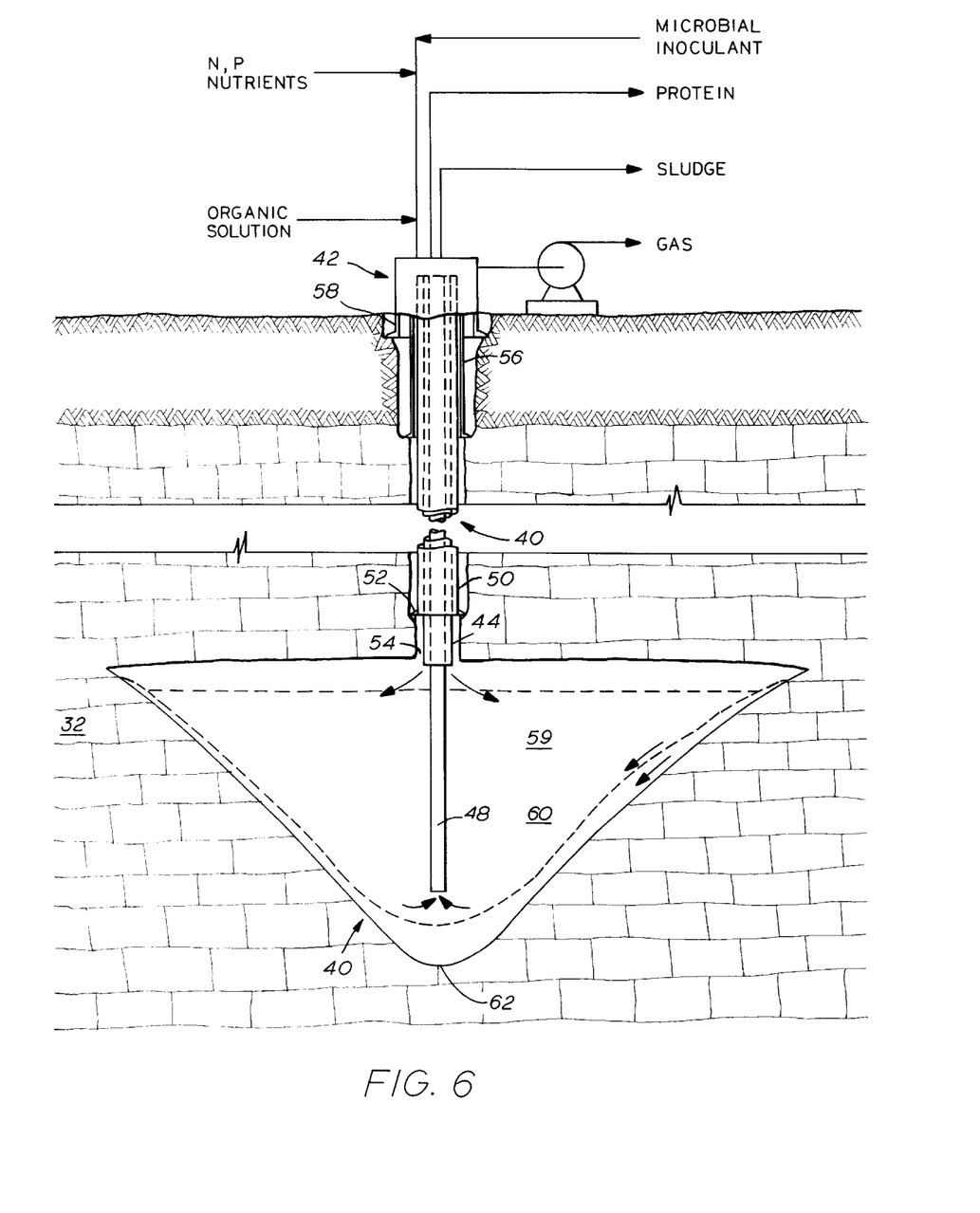
FIG. 6 is a schematic illustration of another embodiment of a subterranean bioreactor of the present invention.
Figure 7:
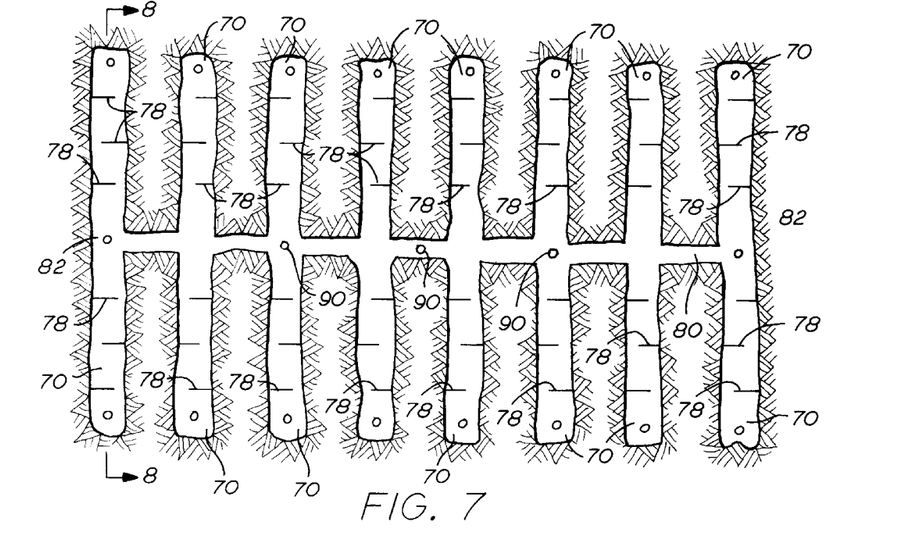
FIG. 7 is a plan view, partially broken away, of yet another embodiment of a subterranean bioreactor of the present invention.
Figure 8:
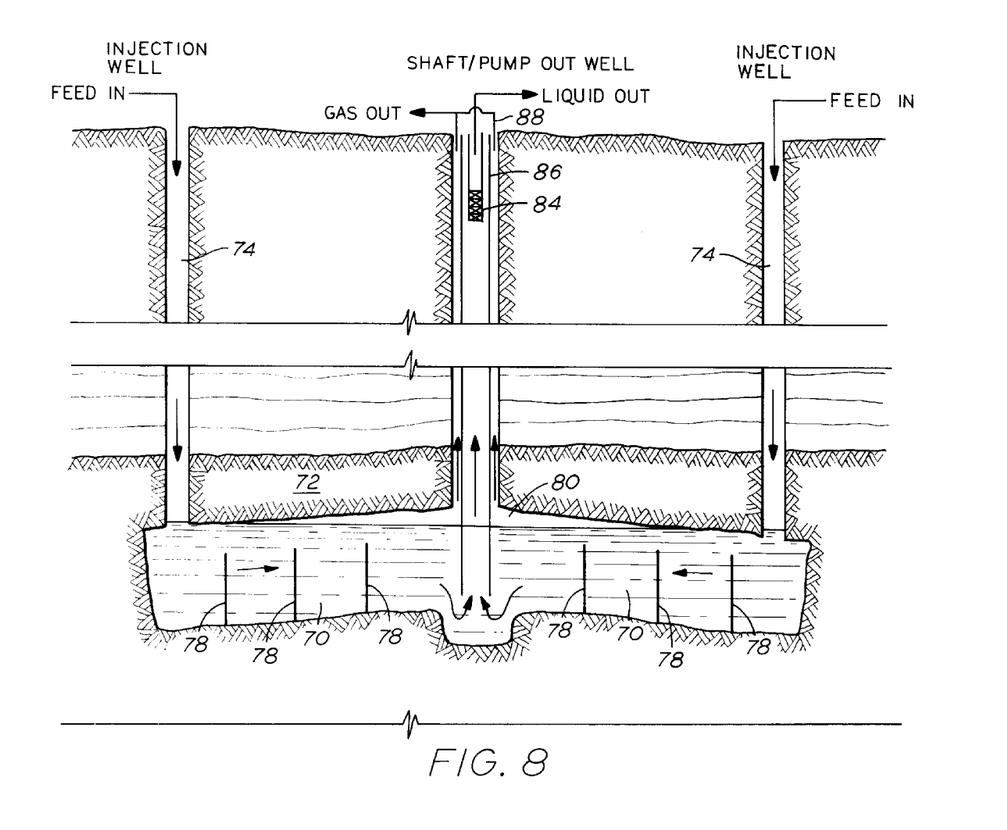
FIG. 8 is a cross-sectional view taken along the lines 8—8 of FIG. 7.

In one embodiment of the invention, a ligninase-treated lignin substrate is gasified by the growth of acid formers and methanogens. The gasification reaction may be carried out in any suitable reactor. However, preferred reactors include cavities in subterranean salt domes (FIGS. 1 through 6) and chambers mined from subterranean rock formations (FIGS. 7 and 8). In salt domes, the cavity may be a naturally occurring subterranean cavity or, more typically, a cavity formed in a subterranean salt formation by well-known methods, such as solution mining. Because most microbially mediated biochemical reactions require moderate temperatures to sustain the microorganisms, it is preferred that the subterranean cavity or chamber be located at a shallow enough depth where the naturally occurring temperature coincides with the optimum temperature for the selected strains of microbes in order that the temperature of the substrate in the cavity can be maintained without cooling. When the present invention is to be performed in a mined chamber in a rock formation, the formation is selected after geological analysis has shown the formation to be suitable for maintaining dimensional integrity of the cavern, as well as to be free of fissures.

Suitable substrates in the gasification method include solutions or pumpable suspensions of any organic material which is reactive with the enzymes and satisfies the proper nutrient requirements for the microorganisms to be employed. It is also essential that the concentration in the substrate of substances toxic to the microorganisms to be employed remain sufficiently low to avoid mortality of the microorganisms. If the organic material to be used in the substrate is deficient in one or more nutrients, it may be rendered suitable for use as a substrate by the addition thereto of the appropriate nutrients. Likewise, it may be possible to remove toxic substances from a material to the extent that it is suitable for use as a substrate.

Depending on the conditions maintained in the substrate in the cavity, the use of virtually any known anaerobic acid forming and methanogenic microorganisms, either naturally occurring or genetically altered under laboratory conditions, are contemplated in the invention. For use in salt domes, the microorganisms must, of course, be salt tolerant. It may in some instances, however, not be possible to maintain the necessary conditions to sustain certain microorganisms in specific substrates and/or liquid media. For example, microorganisms which are sensitive to salt are not suitable for use in the invention if the salt concentration in the substrate or liquid medium is allowed to exceed lethal levels by the dissolving of salt from the walls of the cavity into the substrate. In some instances, however, this problem may be avoided by reducing the residence time of the substrate in the cavity, by reducing the solubility of salt in the liquid medium employed such as, for example, by maintaining a lower temperature or by addition thereto of a nontoxic substance which reduces the solubility of the salt therein, or by use of a liquid medium in which salt is not soluble. In many cases, it is believed that it will be within the capability of those skilled in the art to select or develop microorganisms which are relatively insensitive to salt.

For example, it has been reported that certain cultures are capable of reducing sulfates and producing methane from carbon dioxide in salt marshes. Also, salt-tolerant anaerobic microbes have been recovered by Professor Zeikus (University of Wisconsin) from sediments in the Great Salt Lake, Utah. See, e.g., the article by Zeikus et al., "Isolation and Description of Haloanaerobriem prevalens gen. nov. and sp. nov., an obligately anaerobic halophile common to Great Salt Lake Sediments," *Current Microbiology*, Vol. 9, pp. 225–234 (1983).

There also appear to be other known sources of bacterial cultures to develop a community of organisms to accomplish gasification. They include sewage sludge bacteria; bacteria from areas such as Yellowstone Park which are tolerant of high temperatures and accustomed to a diet of substances including carbon and sulfur (Kargi et al., "Removal of Sulfur Compounds from Coal by the Thermophilic Organism: Sulfolobus Acidocaldarius", *Applied and Environmental Microbiology*, Vol. 44, pp. 878–883, (Oct. 1982); methane producing bacteria found naturally in petroleum formations at depths of from 5,000 to 20,000 feet and deeper, which can be collected from drilling mud at drilling rigs (Donaldson et al., "Conference Focuses on Microbial Enhancement of Oil Recovery", Oil and Gas Journal, Vol. 80, pp. 47–52, Dec. 20, 1982); and bacterial cultures or ecosystems found in fumaroles being investigated by the National Oceanographic Laboratory at La Jolla, Calif. ("Geothermal Deep Sea Marine Life Now Found in Shallow Water," *New York Times*, June, 1984). In an illustrative embodiment described below, the temperature and pH ranges given are for one particular range of organisms insensitive to salt used in a subterranean salt cavity. The conditions described apply to conventional microorganisms which have evolved at or near the earth's surface at conditions similar to those present in the subterranean salt cavity or mined chamber. Depending on the organism selected, other cavities, temperature and pH ranges, and cavity depths could be used.

Following any pretreatment by enzymes or alkali as described below, the substrate is placed in the subterranean cavity by appropriate means, including pumping or gravity flow, through a pipe or other suitable conduit communicating between the cavity and the surface. In the case of solid, insoluble organic material, the substrate may be placed in the cavity in the form of a liquid suspension. A culture of the acid forming and methanogenic microorganisms and any enzyme producing microorganisms may be introduced into the substrate prior to placing it in the cavity. Alternatively, the inoculation may be accomplished by introducing the acid formers, methanogens and/or any enzyme producers directly into the cavity. Although it is contemplated that ligninase per se can be used in the gasification reactor containing acid formers and methanogens, the use of ligninase-producing microbes is preferred as the ligninase source in order to avoid a depletion of ligninase activity which may result from digestion of this enzyme by the acid formers and methanogens.

Once the substrate and microorganisms are in place in the cavity, conditions in the substrate which are suitable for promoting the growth of the microorganisms are controlled. If necessary, the substrate may be heated or cooled by circulation of the substrate from the cavity, heating or cooling the substrate at the surface and returning the heated or cooled substrate to the cavity. Alternatively, a heating or cooling medium may be circulated from the surface into the cavity in indirect heat exchange with the substrate and back to the surface. Preferably, the cavity is located at the proper depth to provide the optimum temperature without heating or cooling.

The pH of the substrate and the cavity may be controlled by periodic or continuous addition thereto of appropriate acids, bases or buffers. Similarly, the nutrients in the substrate may be supplemented by a periodic or continuous addition of deficient nutrients thereto. Likewise, the concentration of toxic substances in the substrate may be controlled by continuous or periodic addition thereto of neutralizing agents or by continuous or periodic removal of the substrate or biochemical products resulting from the growth or action of the microorganisms in the substrate. For example, where the growth of the microorganisms in a liquid substrate results in the formation of insoluble products, sediment may be removed from the lower portion of the cavity by means of a submerged sludge pump.

After the substrate and microorganisms have been in the cavity for a sufficient length of time at the proper conditions, biochemical products which are formed by the growth of the microorganisms in the substrate in the cavity are recovered. The product may be in the form of a gas, miscible or immiscible liquid, or soluble or insoluble solid, or a combination of these forms. Gas is removed from the upper portion of the cavity by means of a fan or compressor. Liquid or solid products are removed by pumping from appropriate depths in the cavity.

In an especially preferred embodiment of the invention, a substrate is anaerobically converted into methane. Preferably, the source of the substrate is coal, and especially lignite. Lignite is the preferred substrate due to its wide availability and its unsuitability for use in place of higher rank coal for certain purposes. Structurally, lignite is characterized by relatively low aromaticity, approximately 60% aromatic. The aromatic clusters of lignite are primarily one and two rings in contrast to bituminous coals having fused ring systems of 3 or more aromatics. In addition, lignite is characterized by a prevalence of oxygen-functional groups such as carboxylate, phenolic and ethereal components. Lignite also contains moisture and ash. The ash-containing portion of lignite contains both inorganic matter, such as calcium and sodium ions, and minerals, such as clay, pyrite and quartz. While the ash and moisture content may vary among lignites, the variation in the organic portion is not significant. As used herein, the term "lignite volatile solids" (LVS) refers to the organic portion of the lignite.

Figure 1:
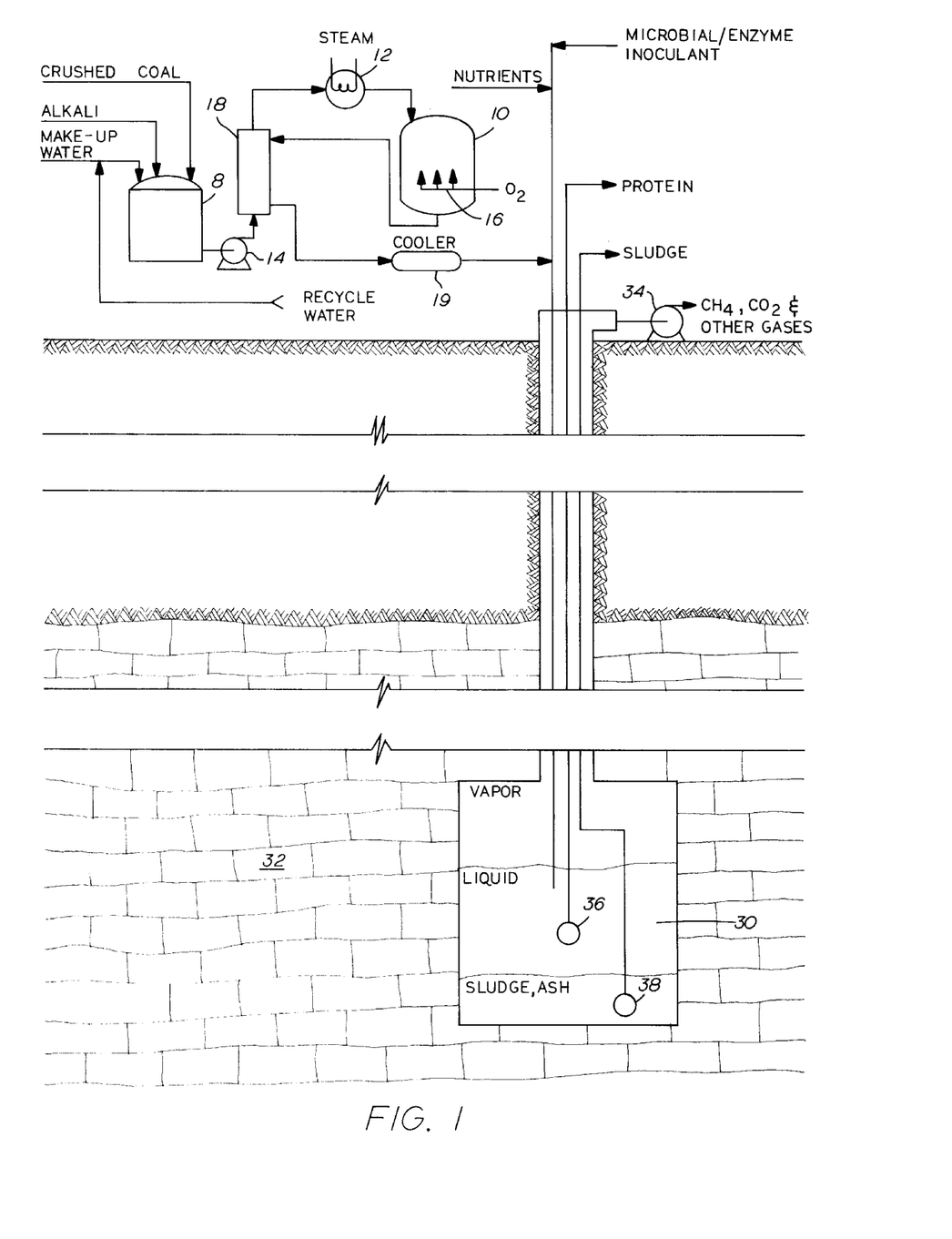
FIG. 1 is a schematic illustration of an embodiment of the method of the present invention in which coal is converted into methane and carbon dioxide in a cavity formed in a subterranean formation.

To render it suitable for use as a substrate, lignite may be contacted in a finely divided state, i.e., substantially all particles passing through a 60 mesh screen, with a hot aqueous alkali solution and with or without oxygen in an alkali hydrolysis vessel or reactor 10 as seen in FIG. 1. The crushed coal and alkali are mixed with water in a slurry prep tank 8 prior to heating and injection into the reactor 10 at elevated pressures. A temperature of from about 150° C. to about 300° C., preferably 200° C. to 250° C., is maintained in vessel 10 by preheating the feed to the reactor through heater 12. Pump 14 provides the pressure for the reaction. For convenience, this type of alkali treatment is referred to as "full" alkali oxidation as a means of distinguishing from the less severe "mild" alkali treatment described below.

The alkali used is not particularly critical and examples include potassium hydroxide, sodium hydroxide or sodium carbonate. The alkali is added to the crushed coal at a rate of from about 0.2 to about 20% on an LVS weight basis. Oxygen can be introduced into vessel 10 by means of sparger 16 or other suitable means. The source of oxygen is preferably air, but may be purified oxygen. The amount of oxygen required is approximately 1 pound per pound LVS. A portion of the heat required to heat the alkali solution and the lignite is provided by the oxidation of the lignite. It should also be understood that in some instances, oxygen need not be used in the pretreatment step. In these situations, no sparger 16 need be present in the vessel 10.

The full alkali oxidation of the lignite may be performed as a batch operation, but is preferably a continuous operation. In a continuous operation in which vessel 10 is continuously stirred, a residence time of 1.5 hours is contemplated to obtain in a conversion of approximately 83% of the organic portion of the lignite into low molecular weight organic matter. The concentration of the organics in the liquid effluent from vessel 10 may be as high as 20% by weight or more. Preferably, the organic concentration is at least about 15% by weight.

The fully alkali-hydrolyzed lignite solution is then cooled to lower the temperature down to about 35–55° C. which is the preferred temperature for conducting the fermentation of the organics into methane. Cooling is performed in heat exchanger 18 preferably by heat exchange with the feed to vessel 10 and/or by cooling water in cooler 19. If desired, undissolved solids may be removed by filtration prior to anaerobic digestion. Alternatively, the solids may be removed from cavity 30 as a sludge which accumulates in the lower portion thereof.

Because lignite is normally deficient in nitrogen and phosphorus, these nutrients are added to the organic solution before it is introduced into the cavity 30. Suitable nutrient supplements are thus provided, which include potash and urea in amounts sufficient to result in a weight ratio of nitrogen to carbon in the organic solution (typically) of about 5:100, and of phosphorus to carbon of about 1:100.

The microbial innoculant is also normally added at this time, in a form which includes ligninase producers, acid formers and methanogens. The ligninase producers hydrolyze or break down larger molecules into smaller ones which are more readily digested by the acid formers and methanogens. The acid formers convert large organic molecules such as proteins, starches, and cellulose into organic acids and are anaerobic and/or facultative in nature. The methanogens convert the organic acids into methane and carbon dioxide and are strictly anaerobic. The microorganisms may be either psychrophilic, mesophilic or thermophilic.

The inoculated organic fluid solution or mixture is then fed via an influent pipe into cavity 30 formed in salt formation 32. The location of solution injection is preferably near the bottom of the cavity 30, but a suitable distance above bottom to allow room for ash and microbial sludge to accumulate. This is done in order to avoid physical removal of these solids during the service life of the cavern. If desired, a packed bed of crushed stone may be deposited on the cavity bottom to provide greater chemical reactant surface.

Conditions in the substrate are maintained such that the growth of the microorganisms therein is promoted. The temperature is maintained from about 10° C. to about 60° C., preferably 10–20° C. for psychrophilic microorganisms, 30–40° C. for mesophilic and 50–60° C. for thermophilic. If necessary, the organic solution or mixture in the cavity may be heated or cooled as described above. The pH is maintained between about 6.5 and about 8.5, preferably between 6.6 and 7.6, and most preferably between 7.0 and 7.2. The pH may be continuously or periodically adjusted by addition of a mixture of acids or bases to the organic solution. However, buffering the organic solution or mixture with alkali at a near neutral pH will normally control the pH.

When the process of the present invention is performed in subterranean salt caverns, the biogasification reaction is preferably carried out in an aqueous broth containing greater than a 10% concentration of sodium chloride. Halophilic microbes are known to operate under anaerobic conditions at concentrations of 10–20% sodium chloride. The use of broths with less than 10% sodium chloride requires special precautions to avoid or minimize leaching of sodium chloride from the cavern walls.

The microorganisms in the inoculated organic fluid solution or mixture are allowed to grow in the cavity for a sufficient period of time to convert a significant quantity of the organics into methane. The length of time required may range from one day to approximately thirty days, depending on the desired conversion rate and the specific substrate and conditions in the cavity. Methane and carbon dioxide are recovered from a vapor space at the top of the cavity through an effluent pipe by means of fan 34. The effluent and influent pipes can be on opposite sides (FIG. 1) of the cavity 30 so that the reacting liquid can be recirculated. The recovered gaseous mixture of methane and carbon dioxide may be subsequently processed to recover purified methane and carbon dioxide according to conventional processing methods.

A protein-rich broth may also be recovered by means of broth pump 36 and used for chemical feedstocks, or recirculation to cavity 30, as desired. Sediment may be removed from the cavity by means of sludge pump 38 or left in the cavity itself as an economical disposal alternative. The sludge contains insoluble lignite and/or solids formed by the growth of the microbes in the organic solution or mixture. The sludge can be disposed of or burned for fuel after dewatering.

In the embodiment set forth in FIG. 1, microbial innoculant in the form of ligninase producers, acid formers and methanogens are added at one time with the cavity 30 functioning as a continuous stirred tank reactor. It should be understood that a staged reactor design could also be used, with the ligninase producers and/or acid formers being injected into a first vessel, whether at the surface or in a separate subterranean cavern or cavity. The acid formers and/or methanogen components of the innoculant are then injected, along with the output of the first vessel, into the cavity 30 which serves as a second stage reactor.

Figure 2:
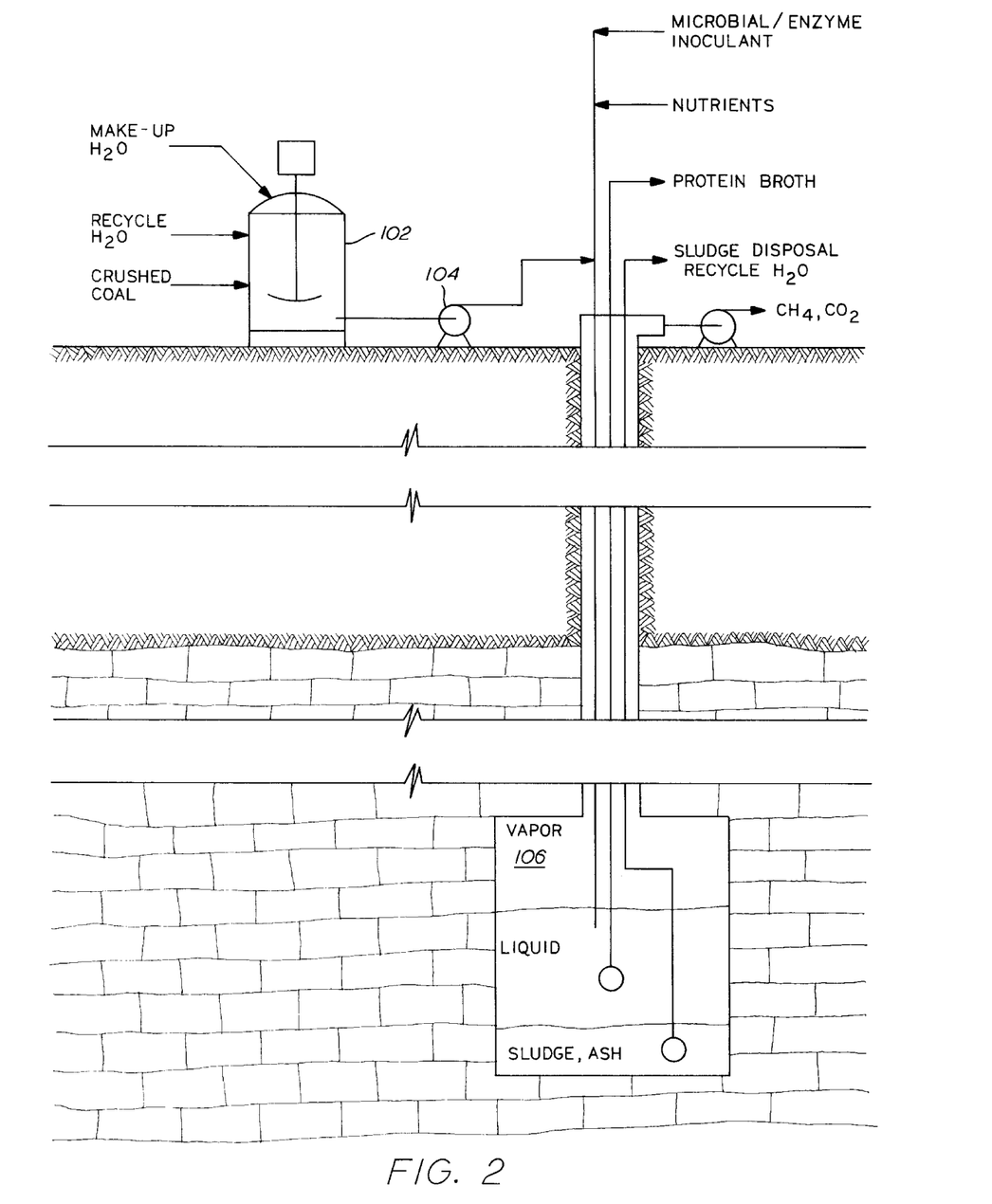
FIG. 2 is a schematic illustration of another embodiment of the method of the present invention in which coal is subjected to methane fermentation in a subterranean bioreactor to which ligninase producing microorganisms are directly added, without alkali pretreatment.

In an alternate embodiment seen in FIG. 2, a slurry of finely divided coal in water is prepared in slurry mixer 102. The slurry is pumped by pump 104 directly to underground cavern bioreactor 106 without alkali pretreatment. To the slurry in cavern reactor 106 are added the nutrients and microbial innoculant for methane fermentation. The microbes preferably include essentially the total microflora from selected termites. The reactor 106 is essentially the same as cavity 30 and is operated in the same manner. The residence time is preferably controlled between one day and thirty days, depending upon cavern design.

Figure 3:
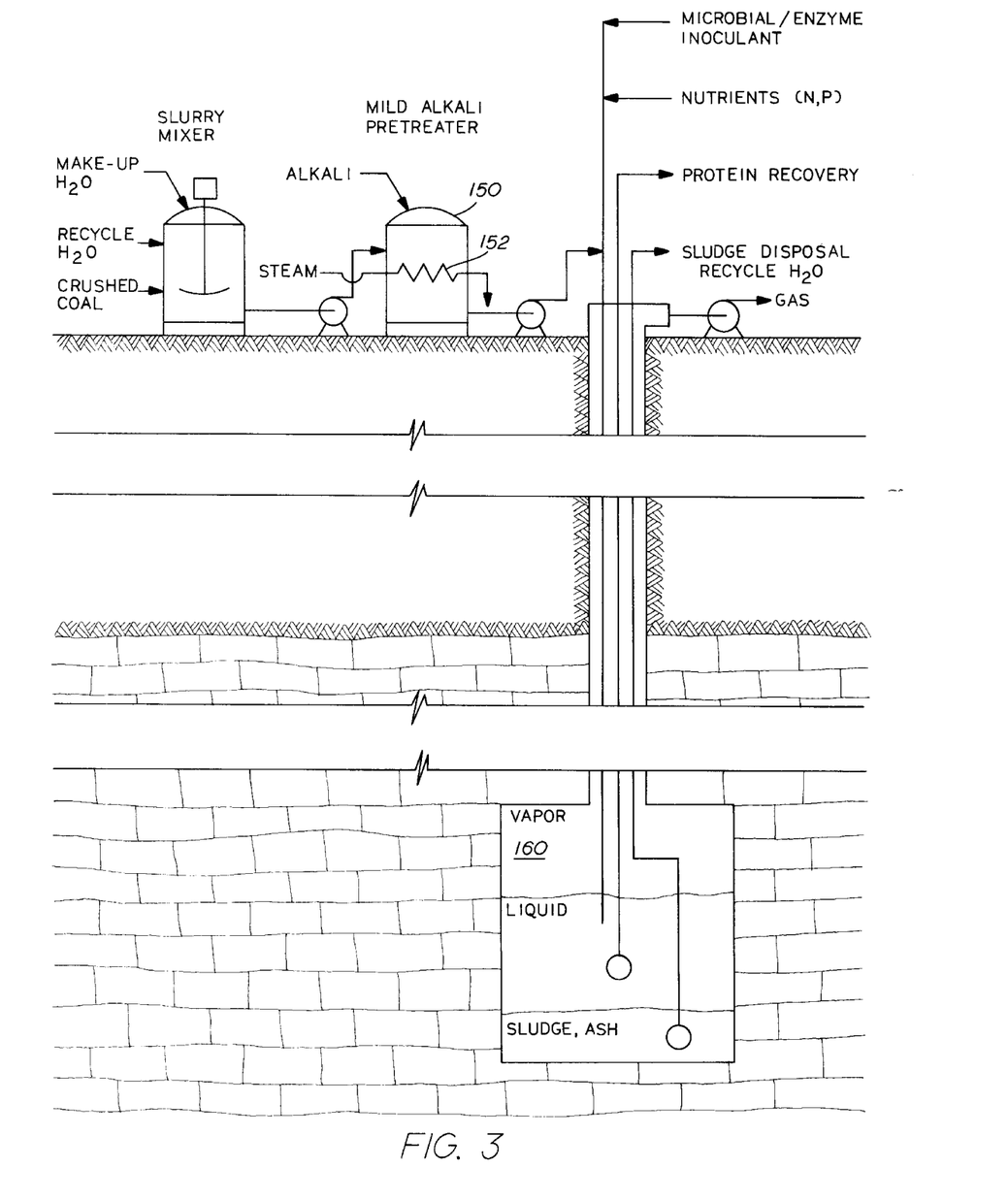
FIG. 3 is a schematic illustration of another embodiment of the present invention in which coal is pretreated with mild alkali before methane fermentation in a subterranean bioreactor containing ligninase.

The embodiment seen in FIG. 3 differs from that of FIG. 2 primarily in that a "mild" alkali treatment is carried out prior to the bioreactor. The crushed coal-water slurry is pumped to alkali pretreatment vessel 150. The pretreatment vessel 150 is equipped with steam coil 152 to rapidly heat the alkali-coal slurry to 150°–300° C., preferably 200°–250° C., preferably in less than three minutes, and especially in less than one minute. Alkali is fed to the pretreatment vessel 150 at a rate of 5–10 percent by weight on an LVS basis. The slurry in contact with the alkali should be maintained at the treatment temperature for a period of time to beneficiate or substantially degrade the coal for ligninase treatment, preferably at least ten seconds, and especially at least one minute. However, the slurry should not be maintained at the treatment temperature for more than about ten minutes, preferably not more than five minutes and especially not more than three minutes to avoid a too extensive hydrolysis of the coal so that less beneficiation of the coal results upon treatment by the ligninase. Following exposure to the treatment temperature, the slurry is rapidly cooled or quenched to near ambient temperature preferably in less than three minutes, and especially in less than one minute.

This mild pretreatment causes the coal particles to at least open or swell, but not necessarily to be broken down to smaller water-soluble fragments as described above in reference to FIG. 1. This enhances the ligninase beneficiation of the coal for the acid formers. The pretreated coal is fed to the cavern bioreactor 160, along with microbial innoculant and nutrients as in FIGS. 1 and 2. The mild alkali pretreatment is more economical than the full alkali pretreatment described above in reference to FIG. 1, yet the opened/swelled coal particles are more readily acted upon by the ligninase producers as a result of the mild alkali pretreatment described here.

Figure 4:
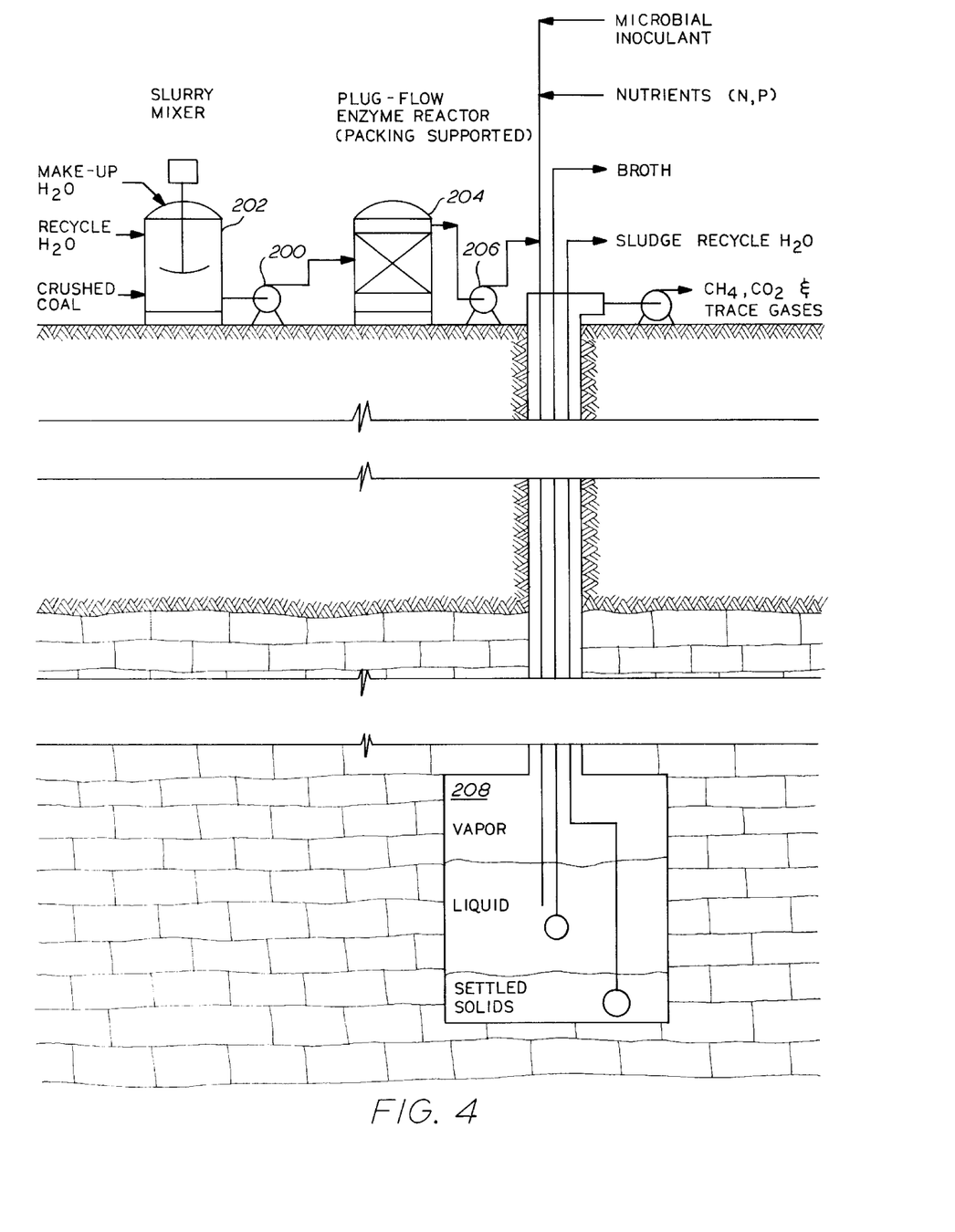
FIG. 4 is a schematic illustration of another embodiment of the method of the present invention in which coal is pretreated with enzyme and then fed to a subterranean bioreactor.

In the embodiment seen in FIG. 4, a slurry of coal in water is pumped by pump 200 from slurry mixer 202 to anaerobic plug flow reactor 204, which may be located on the land surface as shown or in a subterranean cavern (not shown). The anaerobic reactor 204 contains a ligninase source immobilized on a packed bed to convert the larger lignite macromolecules into water-soluble lower molecular weight compounds having substantially one aromatic ring per molecule. A small quantity of immobilized enzyme packing is required as "make up" and must be continually supplied to the reactor. The packing may be, for example, a biomaterial such as calcium alginate or a synthetic material such as polyamide fiber on which ligninase is immobilized, or another substrate suitable for the growth of microorganisms producing ligninase. The enzymatic reactor 204 is maintained at a temperature in the range of from about 20° C. to about 80° C., although temperatures higher or lower than this are contemplated, depending on the thermophilicity of the enzyme employed. As an alternative to the immobilized enzyme packed bed reactor, it is contemplated that the enzyme may be free in solution, in which case, the enzyme must be recovered and recycled, for example, by absorption of the ligninase on a sorbent, and desorption therefrom under conditions unfavorable to absorption, e.g., by changing pH, ionic strength, salt concentration, temperature, or the like. The enzymatic packed bed reactor 204 preferably has a hydraulic residence time of from about 1 to about 100 hours, but shorter or longer residence times may be employed as desired.

The pre-treated substrate (water-soluble single ring aromatic fragments) from the immobilized enzymatic plug flow pretreatment reactor 204 is pumped by pump 206 into a subterranean cavern 208 used as a bioreactor. To this substrate stream is added a microbial innoculant containing acid formers and methanogens and nutrients such as nitrogen and phosphorous compounds. The microbial inoculum is preferably one acclimated from sewage sludge digesters, lake sediment, etc., and need not be derived from termites. The underground reactor 208 may be of a continuous stirred tank type or of a packed bed type, or expanded bed type, i.e., conventional or advanced digester design. Depending upon the geological conditions at the plant site, rock caverns or salt caverns could be used, although the latter implies the use of halophilic methane fermentation. The subterranean cavern 204, therefore, is designed to permit optimum methane fermentation of the organic substrate (water-soluble aromatics obtained by enzymatic breakdown of lignite) into methane and $CO_2$, and other trace gases such as $H_2S$ and $H_2$.

Figure 5:
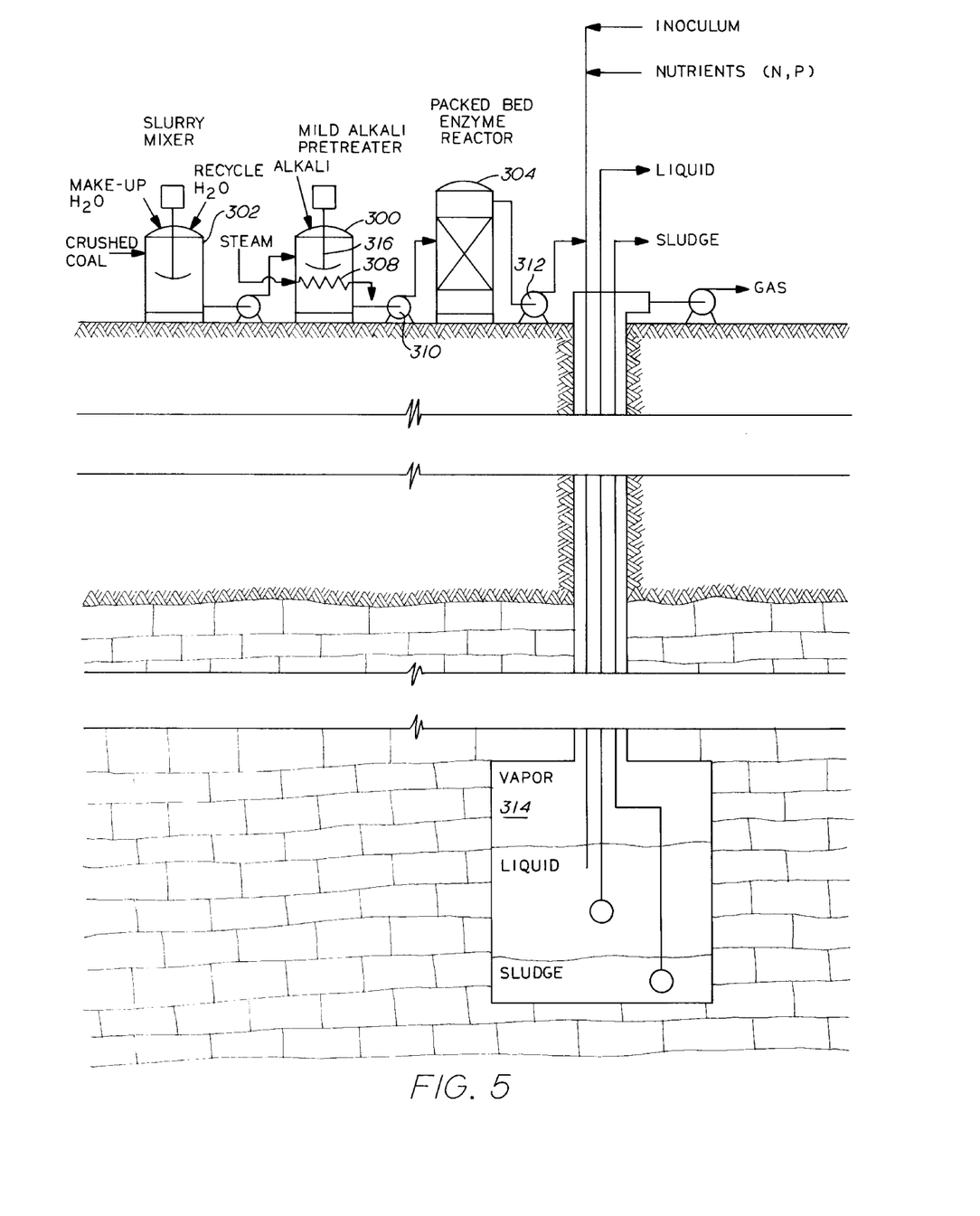
FIG. 5 is a schematic illustration of another embodiment of the invention in which coal is pretreated first with mild alkali, then with enzyme, followed by feeding the pretreated coal to a subterranean biochemical reactor.

The embodiment seen in FIG. 5 is similar to FIG. 4 except that "mild" alkali pretreatment vessel 300 is inserted between slurry mix tank 302 and anaerobic plug-flow reactor 304 containing immobilized enzymes. The alkali pretreater 300 is equipped with agitator 306 and steam heating coil 308. The mild alkali pretreatment opens or swells the polymeric lattice structure of the coal in order to facilitate subsequent enzymatic treatment of the lattice in the reactor 304. The alkali pretreater 300 is operated in the same manner as alkali pretreatment vessel 150 described above.

The coal slurry is pumped by pump 310 from the alkali pretreater 300 to the enzymatic plug-flow reactor 304 where the ligninase cleaves the ether linkages in the coal lattice to produce water-soluble, single ring aromatic compounds. As in FIG. 4, the enzymes may be free in solution (not immobilized), but in this situation the enzymes must be recovered and recycled. It is contemplated that the "mild" alkali pretreatment will enable the plug-flow enzymatic reactor 304 to operate more efficiently and complete the breakdown of the macromolecules of lignite in shorter residence time relative to the embodiment of FIG. 4. The effluent stream from the plug-flow reactor 304 is pumped by pump 312 to cavern fermenter 314 exactly as described in FIG. 4.

In addition to the solution-mined subterranean cavity reactors mentioned in reference to the embodiments of FIGS. 1–5, several alternative reactor designs are contemplated. In the alternative salt dome cavern embodiment of the present invention (FIG. 6), a generally conically shaped cavern 40 is formed in the salt dome formation 32. Cavern 40 functions as a continuously stirred tank reactor, receiving the untreated or alkali hydrolyzed and/or enzymatically pretreated lignite solution, nitrogen and phosphorous nutrients, microbial innoculant and any enzyme from structure like that of FIGS. 1–5, which is for this reason not shown in FIG. 6.

In forming the cavern 40, raw water is fed at a wellhead 42 to a casing 44 of a string 46 of multiple concentric casings. Casing 44 is next innermost of the concentric casing string 46 and contains a longer, innermost wash casing 48. A product casing 50 is located concentrically about casing 44 and is sealed, as indicated schematically at 52, to form an annular pocket 54 in salt formation 32 about casing 44. A conventional intermediate casing 56 and conductor casing 58 complete the casing string 46.

During leaching operations, a compressed gas blanket is present in this pocket 54. A reverse circulation mining technique is used, and the raw water 59 entering cavern 40 from casing 44 mixes with and becomes a part of a brine wash 60 which leaches out the salt formation 32 to form the cavern 40. As leaching proceeds, wash casing 48 is gradually lowered with respect to casing 44, causing the cavern 40 to assume the general shape of a cone with a tip 62 at its lowermost central portion.

Once the cavern 40 has been formed of a suitable size, the brine and water are removed. The inoculated nutrified solution to be fed to the cavern 40 is then injected through the casing 44 until cavern 40 is sufficiently charged. The microbial processes described with respect to FIGS. 1–5 then are allowed to begin, with a cap of methane, carbon dioxide and other product gases accumulating in annular pocket 54. These gases are then withdrawn via product casing 50 by compressor 34. The protein broth formed is withdrawn via wash casing 48. As the gases and broth are removed, new solution is added via casing 44.

An advantage of the conical cavern 40 is that any insoluble solids 64 produced during the biochemical reaction tend to fall and settle on downwardly sloping side walls of cavern 40, tending to migrate slowly toward the tip 62. These solids further coat the sloping walls of the cavern 40, acting as a barrier to inhibit additional leaching during operation of cavern 40 as a continuously stirred tank bioreactor. The solids by moving downwardly also move away from the gas removal pocket 54 at the top of cavern 40, facilitating the gas-liquid separation process.

An alternate embodiment of the present invention uses a mined subterranean cavern, shown in FIGS. 7 and 8, to promote plug flow and thus permit shorter residence time. A number of generally horizontal chambers 70 are mined from a suitable subterranean rock formation 72 by drilling and casing shafts 74 to a suitable depth, typically from two hundred to two thousand feet below the surface. The shafts 74 are then cleared of water and conventional hoists installed in them for transporting miners, equipment and supplies to the area to be mined. The generally horizontal chambers or drifts 70 are then mined out using, for example, the conventional mine, blast and muck technique. In this technique, bench headings are drilled, explosives installed and the rock face is blasted. Rubble produced is then transported to the surface for disposal. A suitable number of baffles 78 are located along the length of the drifts 70, for reasons to be set forth. Further, it is desirable that the drifts 70 slope gently upwardly from the shafts 74, typically on the order of a five percent slope. It should be understood that other percentage slopes could equally as well be used, depending on site conditions, with ranges of from about three percent to about ten percent being generally acceptable.

A transversely extending tunnel 80 is mined or formed to connect inner end portions of aligned drifts 70. A main pump out shaft 82 is formed at each end of the tunnel 80 and a submersible pump 84 is installed in an inner casing 86 to pump protein broth or liquid from the tunnel 80 and drifts 70. An outer casing 88 permits gases produced from the bioreaction which accumulate in an upper portion of the inner ends of drifts 70 and tunnel 80 to be pumped out by a pump of the type shown in FIGS. 5 and 6. A number of pump out wells 90 are formed along the length of the tunnel 80 so that gas and liquid produced in the drifts 70 and tunnel 80 may be extracted and transported to the surface.

In the embodiment of FIGS. 7 and 8, sixteen drifts 70 are shown, each approximately two hundred twenty feet in length. The drifts 70 are about forty feet by forty feet in vertical cross-section in the embodiment shown. This is given only as an example, since length to diameter ratios of from 5:1 to 100:1 may be used depending on process output requirements and geological conditions at the site. The main shafts 82 are located approximately eight hundred feet from each other. The number of pump out wells 90 can range from the three shown to as many as eight or ten, according to process output capacity.

After the drifts 70 have been mined and the baffles 78 installed, a portion of the rubble produced during mining operations is crushed to a suitable size, such as one inch by two inches or so. The crushed rubble so produced is then packed into the drifts 70 to serve as a substrate for the biochemical reaction, which functions as an anaerobic fixed film process. As alternatives to crushed formation rock, gravel or synthetic resin particles or other suitable particles may be used to pack the drifts 70. The packing material can be considered an anaerobic filter.

The input feed stock of inoculated organic fluid solution is then injected into the drifts 70 from injection wells in the shafts 72, travelling through the drifts 70 in a plug flow reaction. The packed drifts 76 function as packed bed bioreactors, with the baffles 78 functioning to increase the flow rate of the reacting fluid solution and promote plug flow.

Alternatively, the reaction may take place in either the form of what is known as a sludge blanket or an expanded bed or fluidized bed anaerobic fixed film digester. In the sludge blanket, a floc of microorganisms occurs and is maintained, further entrapping newly formed microorganisms. In the expanded bed or fluidized bed designs, the particles used for microorganism attachment are of a size and density, relative to the aqueous fermenter fluid, such that they expand or become fluidized. This permits less clogging of the bed by any suspended debris.

The utility of the present invention is demonstrated by way of the following examples:

EXAMPLE 1

Seventy digestive tracts were obtained from the termite species *Nasutitermes nigriceps* by placing the live termites on a glass surface which was in contact with ice to slow the activity of the insects, holding the head of the termite with forceps, and pulling the entire digestive tract from the insect with a second forceps.

The digestive tracts were immediately placed onto a watch glass in 0.5 ml enrichment medium which had been previously prepared from the following ingredients:

| Ingredient | Amount (per 100 ml) |
| --- | --- |
| Yeast Extract | 0.2 |
| Trypticase | 0.2 |
| $K_2HPO_4$ | 0.188 |
| $KH_2PO_4$ | 0.094 |
| KCl | 0.160 |
| NaCl | 0.143 |
| $MgSO_4 \cdot 7H_2O$ | 0.013 |
| $CaCl_2 \cdot 2H_2O$ | 0.008 |
| Pfennig's Metal Solution | 0.1 ml |
| B Vitamin Solution | 0.1 ml |

The enrichment medium was prepared essentially as described in Odelson and Breznak, *Appl. Enviro. Micro.*, vol. 49, pp. 614–621 (1985). Briefly, the ingredients were combined in their respective proportion in distilled water, the pH was adjusted to 6.7–6.8, the mixture was boiled under a nitrogen atmosphere, dispensed as 9.8 ml of the medium into 25 ml test tubes, and autoclaved at 121° C. for 15 minutes, followed by addition of 0.2 ml of sterile cysteine-HCl/$Na_2S$ (1.25% each, w/v) to each test tube.

The Pfenning's Metal Solution and the B Vitamin solution used in the methanogen medium are described above.

The Pfenning's Metal Solution used to prepare the enrichment medium had the following ingredients in distilled water:

| Ingredient | Amount (g/l) |
| --- | --- |
| $ZnSO_4 \cdot 7H_2O$ | 0.1 |
| $MnCl_2 \cdot 4H_2O$ | 0.03 |
| $H_3BO_3$ | 0.3 |
| $COCl_2 \cdot 6H_2O$ | 0.2 |
| $CuCl_2 \cdot 2H_2O$ | 0.01 |
| $NiCl_2 \cdot 6H_2O$ | 0.02 |
| $Na_2MoO_4 \cdot 2H_2O$ | 0.03 |
| $FeCl_2 \cdot 4H_2O$ | 1.5 |

The B Vitamin Solution used to prepare the enrichment medium had the following ingredients in distilled water.

| Ingredient | Amount (g/l) |
|---|---|
| Nicotinic Acid | 2 |
| Cyanocobalamin | 2 |
| Thiamin | 1 |
| p-Aminobenzoic Acid | 1 |
| Pyridoxine | 5 |
| Pantothenic Acid | 0.5 |

The digestive tracts in the 0.5 ml enrichment medium were pipetted into the receiver of a 15 ml Ten Broeck tissue grinder and homogenized with another 0.5 ml of enrichment medium in an oxygen-free atmosphere of 95% nitrogen and 5% carbon dioxide. The homogenate was then used to inoculate various media in 25 ml test tubes. In each test tube was placed 50 $\mu$l of homogenate and medium to a total volume of 10 ml. Each test tube was flushed with nitrogen-:carbon dioxide 95:5, sealed with a rubber septum, and incubated horizontally at 28–30° C.

Three sets of triplicate cultures were established with enrichment medium containing lignite supplements at a concentration of 0.1 percent by weight of lignite solids in the medium. One set of cultures had a lignite supplement mined near Jewett, Tex., which had been pulverized and ball-milled in water at 37.5 percent by weight lignite solids to obtain a dispersion with the consistency of pudding. The lignite supplement in the second set of cultures was prepared by adding 0.27 g sodium hydroxide to each 100 ml of the ball-milled lignite, rapidly heating this mixture to 250° C. in a Parr Instruments Model 5422 pressure reactor, maintaining this temperature for 100 seconds, and rapidly quenching the mixture. The third set of cultures contained the centrifuged supernatant of the briefly heated mixture.

A control set of duplicate cultures was established using methanogen medium which had the following proportion of ingredients in distilled water:

| Ingredient | Amount (per 100 ml medium) |
|---|---|
| Pfennig's Metal Solution | 0.1 ml |
| Pfennig's Mineral Solution | 5.0 ml |
| B Vitarnin Solution | 0.5 ml |
| 0.2% Resazurin Soiution | 0.05 ml |
| Trypticase | 0.2 g |

This methanogen medium was prepared essentially as described in McInerney et al, *Arch. Microbiol.*, vol. 122, pp. 129–135 (1979). Briefly, the ingredients listed above were combined in distilled water in the indicated proportions, the pH was adjusted to 6.8–6.9, the mixture was sterilized by boiling in an atmosphere of $N_2:CO_2$ (95:5) and dispensed in 9.1 ml aliquots to 25 ml test tubes. To each tube was then added 0.7 ml $NaHCO_3$ (5% w/v) and 0.2 ml cysteine-HCl/$Na_2S$ (1.25% each, w/v), followed by regassing with $H_2:CO_2$ 80:20 and innoculation with 50 ml of the termite digestive tract homogenate described above.

The Pfenning's Mineral Solution used to prepare the methanogen medium had the following ingredients in distilled water:

| Ingredient | Amount (g/l) |
|---|---|
| $KH_2PO_4$ | 10.0 |
| $MgCl.6H_2O$ | 6.6 |
| NaCl | 8.0 |
| $NH_4Cl$ | 8.0 |
| $CaCl_2.2H_2O$ | 1.0 |

Typically at one week intervals, gas samples from the headspace of the culture tubes were anaerobically obtained with a hypodermic syringe and analyzed on a Fischer Scientific Model 29 gas partitioner. Approximately once a month, one ml of liquid was transferred from each culture into 10 ml of fresh medium prepared in the same manner. In all samples, and controls, including transferred samples, methane was detected in the first four weeks following inoculation or transfer. These results indicate that termite microflora generate methane in the presence of lignite.

EXAMPLE 2

The procedure of Example 1 was followed using termites of the species *Nasutitermes costalis*. Similar results were obtained, showing that the microflora of this termite species also generate methane in the presence of lignite.

EXAMPLE 3–8

The procedure of Example 1 was followed using termites of the species *Paraneotermes simplicicornis, Pterotermes occidentis, Marginitermes hubbardi, Zootermopsis laticeps, Heterotermes aureus* and *Reticulitermes tibialis*. Depending on the size of the termites, however, from 5 (for larger termites) to 60 (for small termites) digestive tracts were homogenized in 1 ml of enrichment medium. Headspace gas analysis at six weeks post incubation are presented in Table 1 for carbon dioxide and methane relative to total gas.

TABLE 1

| | | Gas Analysis (% of Total) | | | | | | |
|---|---|---|---|---|---|---|---|---|
| | | Control | | Raw Lignite | | Treated Lignite | | Treated Lignite Supernatant | |
| Example | Termite | $CO_2$ | $CH_4$ | $CO_2$ | $CH_4$ | $CO_2$ | $CH_4$ | $CO_2$ | $CH_4$ |
| 3 | P. simplicicornis | 6.1 | 3.1 | 6.6 | 3.8 | 6.3 | 0.5 | 6.6 | 1.7 |
| 4 | P. occidentis | 6.3 | 1.9 | 7.7 | 4.3 | 6.3 | 1.7 | 5.9 | 0.2 |
| 5 | M. hubbardi | 5.2 | 0.7 | 6.7 | 4.7 | 6.4 | 4.3 | 6.1 | 0.9 |
| 6 | Z. laticeps | 6.4 | 2.0 | 6.9 | 3.7 | 6.9 | 3.9 | 7.2 | 3.0 |
| 7 | H. aureus | 5.8 | 0 | 6.1 | 1.2 | 6.1 | 0 | 6.9 | 0 |
| 8 | R. tibialis | 5.7 | 1.5 | 7.2 | 1.5 | 5.3 | 1.7 | 5.3 | 0.8 |

These results indicate that microflora of these termites generate methane in the presence of lignite, and that more methane is generally generated by the microflora in the presence of ball-milled lignite and/or lignite subjected to mild alkaline hydrolysis than in the absence of lignite or in the presence of the supernatant from lignite treated by mild alkaline hydrolysis.

EXAMPLE 9

Figure 9:
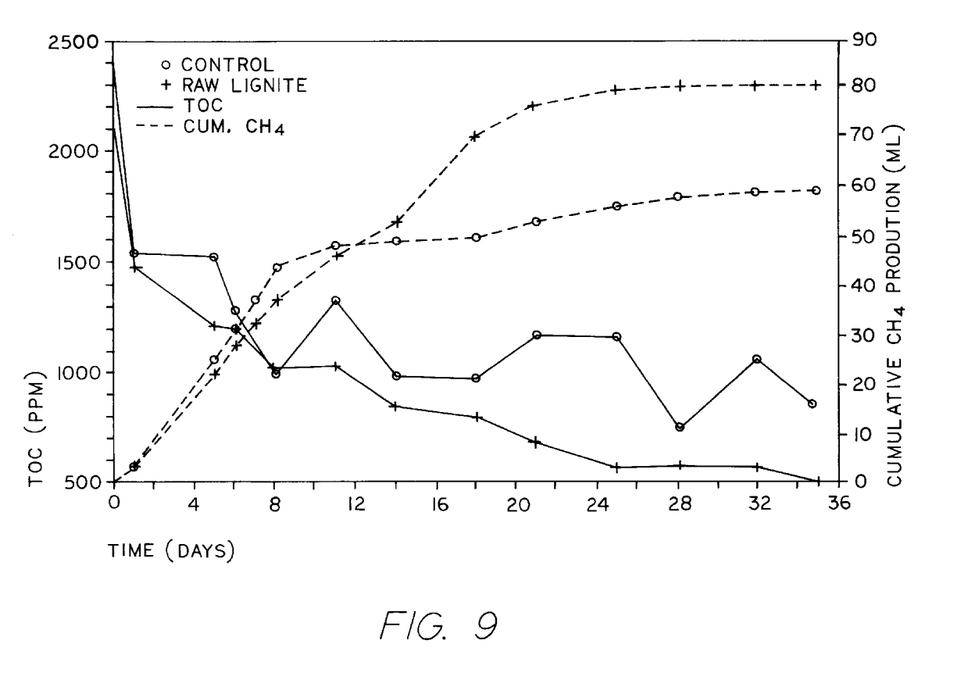
FIG. 9 graphically illustrates methane production and carbon consumption by termite microflora in the presence and absence of lignite volatile solids as described in Example 9.

Ten ml of culture from the samples of Example 1 prepared with ball-milled lignite was inoculated into 90 ml of fresh enrichment medium, to which 340 ml of ball-milled lignite supplement (120 mg lignite solids) had been added, in a 160 ml serum bottle in triplicate cultures. A second set of triplicate cultures was established as controls using enrichment medium without lignite. Of the 120 mg lignite solids in the samples containing lignite, 87 mg was lignite volatile solids. The bottles were flushed with nitrogen, sealed with rubber septa, and maintained in a shaker bath at 37° C. Periodically at intervals of one day or more, gas and liquid samples were withdrawn and respectively analyzed for methane as described in Example 1, and for total organic carbon ("TOC") using a Dohrmann DC-80 carbon analyzer. The averaged results of each triplicate set of cultures are presented in FIG. 9. Methane production and TOC consumption in both sets of cultures proceeded at about the same rate for approximately two weeks. Thereafter, the lignite-containing cultures began producing relatively more methane than the controls, and methane production declined progressively until the cultures were concluded on the thirty-fifth day. The cumulative methane production observed in the lignite-containing bottles exceeded that of the controls by 22.5 ml. Stoichiometrically, the metabolism of all of the lignite to methane and carbon dioxide would have produced 36.6 ml methane. Thus, this result indicates that approximately two-thirds of the lignite volatile solids were converted to methane, and demonstrates that a significant fraction of lignite volatile solids can be biochemically converted into methane fuel gas by anaerobic termite microflora.

While the preferred methods are illustrated in the foregoing description, many variations in the size, shape and materials, as well as in the details of the illustrated method, will occur to those skilled in the art. It is intended that all such variations which fall within the scope and spirit of the appended claims be embraced thereby.

We claim:
1. A method for producing methane from coal comprising:
homogenizing termite digestive tracts to produce a homogenate;
incubating a coal substrate in an incubation medium comprising said homogenate and methanogens, said methanogens selected from the group consisting of methanogens of the homogenate and exogenous methanogens under anaerobic conditions sufficient to generate methane; and
recovering methane from said incubation medium.

2. A method for producing methane from coal comprising:
homogenizing termite digestive tracts to produce a homogenate;
culturing said homogenate in bacterial enrichment medium to produce homogenate-derived microflora;
incubating a coal substrate in an incubation medium containing said homogenate-derived microflora under conditions sufficient to generate methane; and
recovering methane from said incubation medium.

3. The method of claim 2, wherein said coal is lignite.

4. The method of claim 2, wherein said termite is selected from the group consisting of:
*Nasutitermes nigriceps, Nasutitermes costalis, Marginitemes hubbardi, Paraneotermes simplicicornis, Reticulitermes tibialis, Heterotermes aureus, Zootermopsis latiseps,* and *Pterotermes occidentis.*

5. The method of claim 4, wherein said termite is *Nasutitermes nigriceps* or *Zootermopsis latiseps.*

6. The method of claim 2, wherein said incubation medium further comprises acid forming microorganisms, methanogenic microorganisms or combinations thereof.

7. The method of claim 6, wherein methanogenic microorganisms are added to the incubation medium.

8. The method of claim 7, wherein said methanogens are added substantially simultaneously with said termite derived microflora.

9. The method of claim 7 wherein said incubation with termite-derived microflora precedes addition of said methanogens.

* * * * *